United States Patent
Goodwin et al.

(10) Patent No.: US 10,378,098 B2
(45) Date of Patent: *Aug. 13, 2019

(54) METHODS FOR OPTIMIZED PRODUCTION OF MULTILAYER METAL/TRANSPARENT CONDUCTING OXIDE (TCO) CONSTRUCTS

(71) Applicant: Materion Corporation, Mayfield Heights, OH (US)

(72) Inventors: Kevin V. Goodwin, Torrington, CT (US); Robert R. Newton, West Simsbury, CT (US); Peter J. Asiello, Boston, MA (US); Ian S. Tribick, Groton, MA (US)

(73) Assignee: MATERION CORPORATION, Mayfield Heights, OH (US)

( * ) Notice: Subject to any disclaimer, the term of this patent is extended or adjusted under 35 U.S.C. 154(b) by 512 days.

This patent is subject to a terminal disclaimer.

(21) Appl. No.: 15/074,539

(22) Filed: Mar. 18, 2016

(65) Prior Publication Data

US 2016/0274050 A1    Sep. 22, 2016

Related U.S. Application Data

(60) Provisional application No. 62/208,271, filed on Aug. 21, 2015, provisional application No. 62/208,257, filed on Aug. 21, 2015, provisional application No. 62/134,791, filed on Mar. 18, 2015, provisional application No. 62/134,784, filed on Mar. 18, 2015.

(51) Int. Cl.
| | | |
|---|---|---|
| *G01N 27/403* | (2006.01) | |
| *C23C 14/34* | (2006.01) | |
| *C23C 14/02* | (2006.01) | |
| *C23C 14/08* | (2006.01) | |
| *C23C 14/20* | (2006.01) | |
| *C23C 14/56* | (2006.01) | |
| *G01N 27/327* | (2006.01) | |

(52) U.S. Cl.
CPC .......... *C23C 14/3464* (2013.01); *C23C 14/02* (2013.01); *C23C 14/086* (2013.01); *C23C 14/205* (2013.01); *C23C 14/562* (2013.01); *G01N 27/3272* (2013.01)

(58) Field of Classification Search
CPC ..... G01N 27/327–3272; G01N 27/403; G01N 27/333

See application file for complete search history.

(56) References Cited

U.S. PATENT DOCUMENTS 5,667,853 A    9/1997    Fukuyoshi
5,849,208 A    12/1998   Hayes et al.
(Continued)

OTHER PUBLICATIONS

Lee et al., "Characteristic difference between ITO/ZrCu and ITO/Ag bi-layer films as transparent electrodes deposited on PET substrate," Applied Surface Science 257 (2010) 239-243 (Year: 2010).*

*Primary Examiner* — Alexander S Noguerola
(74) *Attorney, Agent, or Firm* — Fay Sharpe LLP

(57) ABSTRACT

The present disclosure relates to processes and apparatuses for optimizing the single pass production of multilayer constructs including metal/transparent conducting oxide (TCO) multilayers. Articles created from such methods are also disclosed. In particular, multilayer constructs are used as an electrochemical test strip, such as a biosensor, and will be described with particular reference thereto.

15 Claims, 2 Drawing Sheets

(56) References Cited

U.S. PATENT DOCUMENTS

| | | | |
|---|---|---|---|
| 6,179,979 B1 * | 1/2001 | Hodges | C12Q 1/004 204/192.14 |
| 6,662,439 B1 | 12/2003 | Bhullar | |
| 6,805,780 B1 | 10/2004 | Ryu et al. | |
| 7,005,857 B2 | 2/2006 | Stiene et al. | |
| 7,041,210 B2 * | 5/2006 | Hodges | G01N 27/3272 205/775 |
| 7,060,192 B2 | 6/2006 | Yuzhakov et al. | |
| 7,073,246 B2 | 6/2006 | Bhullar et al. | |
| 7,294,246 B2 | 11/2007 | Gundel et al. | |
| 7,386,937 B2 | 6/2008 | Bhullar et al. | |
| 7,431,820 B2 | 10/2008 | Hodges | |
| 7,465,597 B2 | 12/2008 | Wegner et al. | |
| 7,470,533 B2 | 12/2008 | Xu et al. | |
| 7,476,827 B1 | 1/2009 | Bhullar et al. | |
| 7,604,721 B2 | 10/2009 | Groll et al. | |
| 7,626,401 B2 | 12/2009 | Dreibholz et al. | |
| 7,892,849 B2 | 2/2011 | Burke et al. | |
| 7,943,022 B2 | 5/2011 | Teodorczyk et al. | |
| 7,955,856 B2 | 6/2011 | Neel et al. | |
| 8,083,884 B2 | 12/2011 | Edelbrock | |
| 8,119,414 B2 | 2/2012 | Burke et al. | |
| 8,206,565 B2 | 6/2012 | Groll et al. | |
| 8,211,632 B2 | 7/2012 | Petyt et al. | |
| 8,222,044 B2 | 7/2012 | Bhullar et al. | |
| 8,273,226 B2 | 9/2012 | Edelbrock | |
| 8,326,393 B2 | 12/2012 | Kotzan et al. | |
| 8,468,680 B2 | 6/2013 | Joseph | |
| 8,551,308 B2 | 10/2013 | Bhullar et al. | |
| 8,603,308 B2 | 12/2013 | Bhullar et al. | |
| 8,793,865 B2 | 8/2014 | Joseph | |
| 8,852,423 B2 | 10/2014 | Liao | |
| 2003/0193289 A1 | 10/2003 | Shirakawa | |
| 2009/0194416 A1 | 8/2009 | Hsiung | |
| 2011/0031119 A1 * | 2/2011 | Hsiao | C23C 14/042 204/416 |
| 2012/0308807 A1 | 12/2012 | Edwards | |
| 2014/0070338 A1 | 3/2014 | Wang | |

* cited by examiner

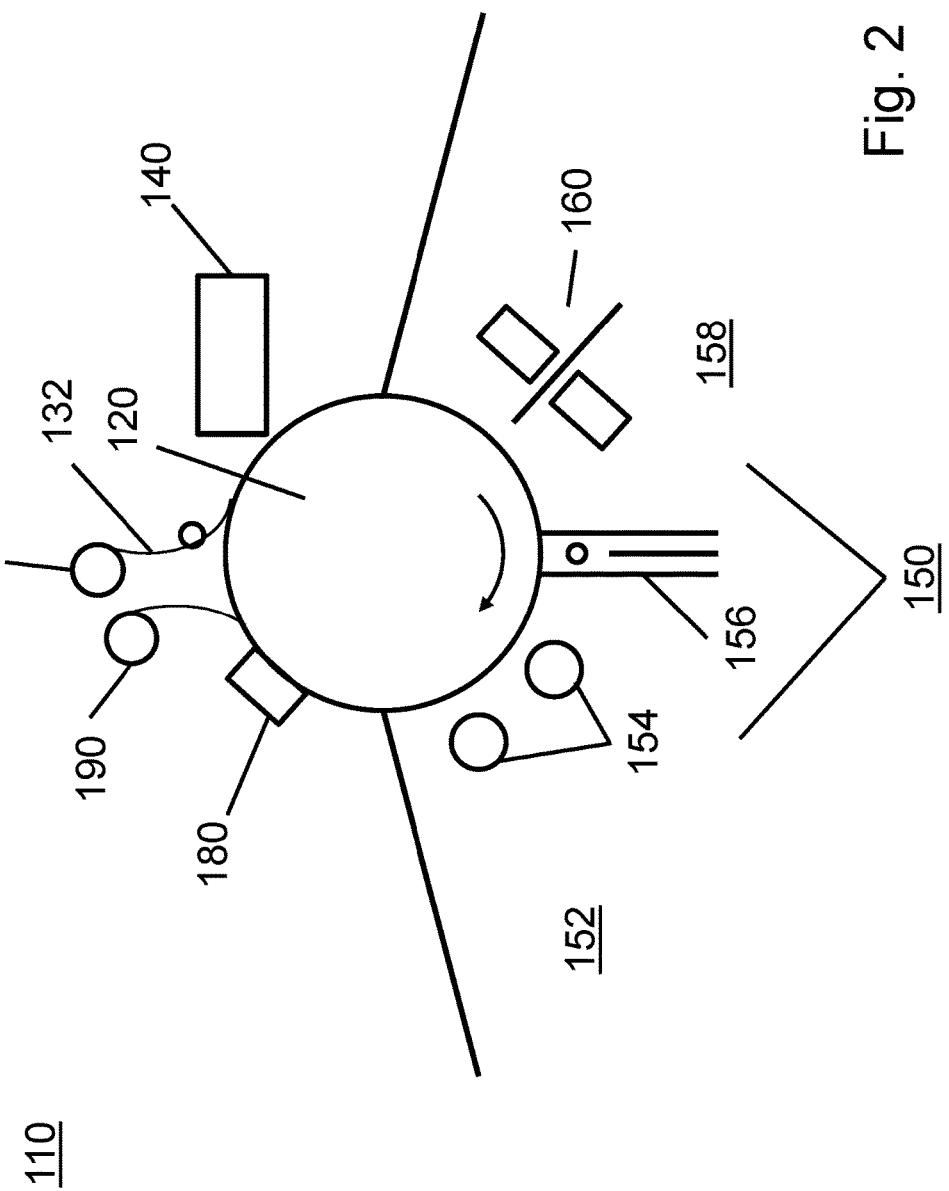

METHODS FOR OPTIMIZED PRODUCTION OF MULTILAYER METAL/TRANSPARENT CONDUCTING OXIDE (TCO) CONSTRUCTS

CROSS-REFERENCE TO RELATED APPLICATIONS

This application claims priority to U.S. Provisional Patent Application Ser. No. 62/208,257, filed on Aug. 21, 2015; U.S. Provisional Patent Application Ser. No. 62/208,271, filed on Aug. 21, 2015; U.S. Provisional Patent Application Ser. No. 62/134,791, filed on Mar. 18, 2015; and U.S. Provisional Patent Application Ser. No. 62/134,784, filed on Mar. 18, 2015, the disclosures of which are hereby fully incorporated by reference.

BACKGROUND

The present disclosure relates to materials and processes for producing multilayer constructs useful for forming electrochemical test strips, as well as devices, such as medical devices, utilizing the same. In particular, multi-layer constructs comprising a non-conductive substrate layer, a conductor layer, and an oxidized Transparent Conducting Oxide (TCO) protective layer are provided. The multi-layer constructs so produced impart superior electrochemical response while maintaining desired mechanical properties, and will be described with particular reference thereto. However, it is to be appreciated that the present disclosure is also amenable to other like constructs and applications.

The present disclosure also relates to processes and apparatuses for optimizing the single pass production of multilayer constructs including metal/Transparent Conducting Oxide (TCO) multilayers. In particular, multilayer constructs are used as an electrochemical test strip, such as a biosensor, and will be described with particular reference thereto. However, it is to be appreciated that the present disclosure is also amenable to other like processes and apparatuses.

Electrochemical test strips can be used in several applications, such as various metering devices for testing and/or determining certain characteristics and/or the presence of analytes in a specimen. In this regard, the test strips can be used as biosensors for measuring the amount of an analyte (e.g., glucose) in a biological fluid (e.g., blood). For example, a glucose biosensor is an analytical device for detecting the analyte, glucose, in the blood. These biosensors use a redox enzyme (e.g., glutathione peroxidases (GPX), nitric oxide synthase (eNOS, iNOS, and nNOS), peroxiredoxins, super oxide dismutases (SOD), thioredoxins (Trx), and the like) in a reagent layer, as the biological component responsible for the selective recognition of the analyte of interest (e.g., glucose).

The biological fluid sample is introduced into the reagent layer of a reaction chamber of the test strip. The test strip is connected to a measuring device such as a meter for analysis using the test strip's electrodes. The analyte in the sample undergoes a reduction/oxidation reaction at the working electrode (where the redox enzyme is located) while the measuring device applies a biasing potential signal through the electrodes of the test strip. The redox reaction produces an output signal in response to the biasing potential signal. The output signal usually is an electronic signal, such as potential or current, which is measured and correlated with the concentration of the analyte in the biological fluid sample.

Electrochemical test strips of this type are made from multilayer constructs. An important feature of these multilayer constructs is that their materials have a reduced sensitivity to heat, humidity and degradation, while maintaining mechanical robustness and good electrical conductivity. These materials are desirably less affected by environmental factors such as air and water, and are mechanically robust while maintaining electrochemical preferentiality.

It would be desirable to develop new methods and processes to produce fully-fabricated multilayer constructs for use in sensor applications. This could result in ready-made multilayer constructs having improved electrochemical and mechanical properties, which could be used in biosensors for several different applications.

BRIEF DESCRIPTION

The present disclosure relates to electrochemical test strips including multilayer constructs having a substrate layer, a metal conductor layer, and an oxidized Transparent Conducting Oxide (TCO) protective layer. The electrochemical test strip may also include a further reagent layer and an optional cover layer, among others. The TCO protective layer advantageously imparts electrochemical preferentiality and mechanical stability over a single layer construction compared to pure metal conductors or metal alloy conductors that are presently used in the industry. The metal conductive layer can have patterns formed in-line through masked deposition or lithography, or formed off-line through laser ablation. The resulting patterns include at least one electrode having desired physical and/or electrical properties.

Along these lines, disclosed in various embodiments are multilayer constructs having a substrate layer having a top surface and a bottom surface, a metal conductive layer formed on the top surface of the substrate layer, and a protective layer deposited on top of the metal conductive layer.

In some embodiments, the metal conductive layer and the TCO protective layer are processed to include patterns on their surfaces. In other embodiments, the metal conductive layer and the TCO protective layer have substantially continuous surfaces.

In various embodiments, the patterns fabricated from the metal conductive layer and/or TCO protective layer include at least one electrode. The patterns and/or electrodes are formed by masked deposition in some embodiments. In other embodiments, the at least one electrode and/or pattern is formed by laser ablation. In still other embodiments, the at least one electrode and/or pattern is formed by lithography.

In some embodiments, the metal conductive layer is a metal alloy. The metal alloy can have a resistivity of less than 100 ohms/sq at a preferred thickness of about 10 nanometers to about 100 nanometers. The alloy also desirably presents an abrasion resistance of less than a 2% change in resistance after ten (10) insertions into a standard clip system. In particular embodiments, the alloys are nickel-based alloys. The nickel-based alloy may further include chromium, molybdenum, cobalt, ruthenium, tungsten, or vanadium. In other particular embodiments, the metal alloy is a cobalt-based super-alloy. In further particular embodiments, the metal alloy is an indium or tin-based alloy.

In other embodiments, the metal conductive layer is a pure metal. The pure metal can be gold, platinum, palladium, and iridium, for example.

In still further embodiments, an apparatus for producing a multilayer construct at a high speed in a single pass is disclosed. The apparatus includes a rotary drum for unwinding and or providing a substrate layer. A Radio Frequency (RF) plasma pretreater then treats the substrate layer prior to the deposition of a thin film metal conductor layer followed by the deposition of the protective TCO layer. This is done in a chamber having a metal sputtering zone and a follow-up TCO sputtering zone separated by a seal. A dual cathode in the metal sputtering zone deposits the thin film metal conductor layer on the substrate layer. A pattern may also be utilized to form an electrode. An AC sputtering option in the TCO sputtering zone subsequently deposits a TCO protective layer on the thin film metal conductor layer at a high speed forming the multi-layer construct. The multi-layer construct may then be joined with a reagent layer and an optional cover layer to form an electrochemical test strip.

This type of construction is less susceptible to both electrochemical and mechanical degradation and offers a lower cost solution having a mechanical and electrochemical advantage.

Disclosed in other embodiments are processes and apparatuses for optimizing the single pass production of multilayer constructs including metal/transparent conducting oxide (TCO) multilayers useful for sensor applications. The processes advantageously permit expedient production of a mixed multilayer construct and provide a clean contact surface between the metal and TCO and provide and optimal TCO layer when compared with multilayer constructs prepared by other methods.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 2 is a front view of an exemplary device for constructing a multilayer construct of the present disclosure.

DETAILED DESCRIPTION

Figure 1:
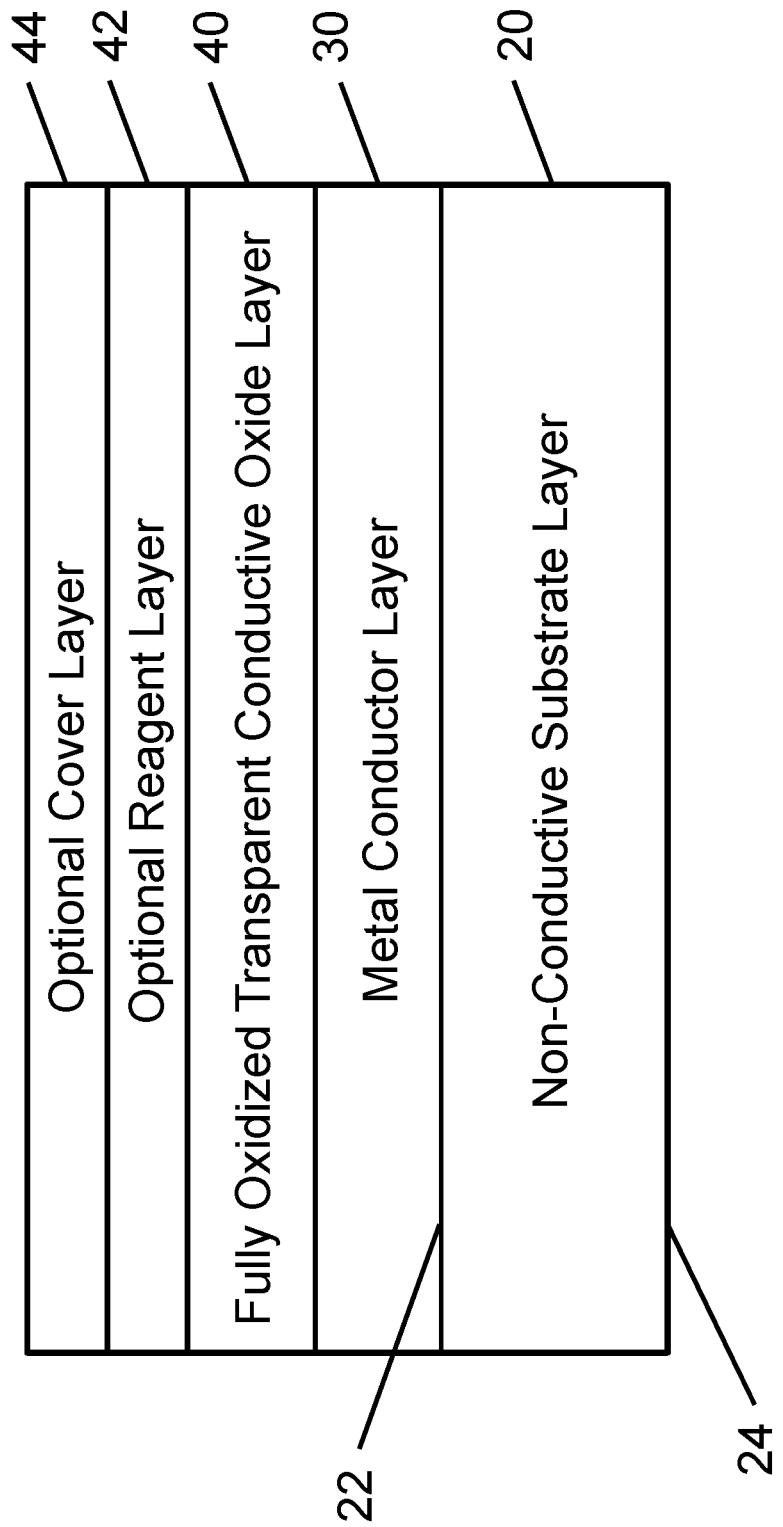
FIG. 1 is a cross-sectional view of an exemplary multilayer construct of the present disclosure.

A more complete understanding of the components, processes and apparatuses disclosed herein can be obtained by reference to the accompanying drawings. These figures are merely a schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can carry without changing the basic function of that value. When used with a range, "about" also discloses the range defined by the absolute values of the two endpoints, e.g., "about 2 to about 4" also discloses the range "from 2 to 4." The term "about" may refer to plus or minus 10% of the indicated number.

A test strip or biosensor is typically formed from: (1) a substrate; (2) a pair of electrodes; and (3) a reagent layer that reacts with the analyte, and generally contains the redox enzyme and electron mediators.

FIG. 1 is a cross-sectional view of a multilayer construct 10 from which an electrochemical test strip can be made. The multilayer construct 10 has a substrate layer 20, a metal conductor layer 30, and a protective transparent conducting oxide (TCO) layer 40. The substrate layer has a top surface 22 and a bottom surface 24. The conductor layer 30, and TCO protective layer 40 are coated or deposited onto the top surface 22 of the substrate 20, while the bottom surface 24 of the substrate remains free of additional layers. One or more additional layers, such as reagent layers 42 and/or cover layers 44, may be added to the multi-layer construct over the TCO protective layer 40 to form an electrochemical test strip.

The substrate 20 is generally made of a non-conductive material, preferably a polymer web. Such materials include plastics, for example polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

The metal conductive layer 30 can be a pure metal, which can be formed on substrate 20 by any method known in the art, such as by sputtering. The pure metal conductor layer 30 can be any suitable pure metallic conductor. Examples of pure metals include aluminum, antimony, barium, beryllium, bismuth, boron, cadmium, cerium, chromium, cobalt, copper, erbium, gadolinium, gallium, germanium, gold, hafnium, indium, iridium, iron, lanthanum, lead, magnesium, manganese, molybdenum, neodymium, nickel, niobium, osmium, palladium, platinum, praseodymium, rhenium, rhodium, ruthenium, samarium, selenium, silicon, silver, tantalum, tellurium, terbium, tin, titanium, tungsten, vanadium, ytterbium, yttrium, zinc, and zirconium. Preferably, the pure metal conductor includes aluminum, cobalt, copper, gallium, gold, indium, iridium, iron, lead, magnesium, nickel, niobium, osmium, palladium, platinum, rhenium, rhodium, selenium, silicon, silver, tantalum, tin, titanium, tungsten, uranium, vanadium, zinc, zirconium and mixtures thereof. Most preferably, the pure metal conductor includes gold, platinum, palladium, ruthenium, and iridium.

Generally, a pure metal is defined as one composed entirely of a single element. Those skilled in the art, however, will recognize that due to the difficulty in removing all traces of other elements or contaminants, a pure metal may also refer to one containing only unavoidable contaminants, impurities, etc.

These metals can be used to provide physical and electrical property advantages when used with specific systems, such as electrochemical test strips. In such systems, the metal conductive layer 30 can be processed to include at least one pattern formed from the conductive layer. The pattern can be an electrode formed on the pure metal conductor layer 30 by scribing, scoring, shadow masking, laser ablating, or lithography. Scribing or scoring may be done by mechanically scribing the pure metal conductor layer. The pure metal conductive layer 30 can also be provided without any pattern formed thereon. That is, the pure metal conductive layer 30 can be provided with substantially continuous surfaces.

The metal conductive layer 30 can also be a custom metal alloy instead of a pure metal. The custom metal alloy desirably increases the conductive layer's resistance to deformation and decreases cost, while desired electrical conductivity properties can be maintained.

The metal alloy itself can be a binary, tertiary, or quaternary alloy of suitable metals. In particular embodiments, the alloy contains nickel in combination with elements such as aluminum, chromium, molybdenum, niobium, titanium, tantalum, vanadium, rhenium, ruthenium, hafnium, tungsten, cobalt, boron, yttrium, platinum (Pt), palladium (Pd), rhodium (Rh), iridium (Ir), and/or osmium (Os). The alloy may contain about 10 atomic percent (at %) to about 75 at % of nickel, and about 25 at % to about 90 at % of other elements. Any combination of one or more of the other elements is contemplated. The alloy may be formed by in-situ sputtering. Desirably, one would fabricate a sputtering target from the alloy, as this allows deposition uniformity to be maintained.

In other embodiments, the alloy contains cobalt in combination with elements such as nickel, aluminum, chromium, molybdenum, niobium, titanium, tantalum, vanadium, rhenium, ruthenium, hafnium, tungsten, boron, yttrium, platinum (Pt), palladium (Pd), rhodium (Rh), iridium (Ir), and/or osmium (Os). The alloy may contain about 10 atomic percent (at %) to about 75 at % of cobalt, and about 25 at % to about 90 at % of other elements. Any combination of one or more of the other elements is contemplated. The alloy may be formed by in-situ sputtering. Desirably, one would fabricate a sputtering target from the alloy, as this allows deposition uniformity to be maintained.

In particular embodiments, the elemental additions in the nickel-based super-alloy are gamma prime (γ') formers such as aluminum, titanium, niobium, tantalum, and hafnium. Desirable properties from gamma prime nickel-based super-alloys can include long-time stability and added ductility imparting strength without lowering fracture toughness.

In other embodiments, the elemental additions in the nickel-based super-alloy include carbon combined with carbide formers such as chromium, molybdenum, tungsten, niobium, tantalum, and titanium. Desirable properties from carbide strengthened nickel-based super-alloys can include the formation of grain boundaries which increase rupture strength at high temperature.

In further particular embodiments, the elemental additions in the cobalt-based super-alloy include carbon combined with carbide formers such as chromium, molybdenum, tungsten, niobium, tantalum, and titanium. Desirable properties from cobalt-based super-alloys hardened by carbide precipitation include hot corrosion resistance, oxidation resistance, and thermal fatigue resistance and weldability.

Alternatively, the metal alloy may be an indium alloy that contains indium in combination with elements such as oxygen, tin, nickel, cobalt, aluminum, chromium, molybdenum, niobium, titanium, tantalum, vanadium, rhenium, ruthenium, hafnium, tungsten, boron, yttrium, platinum (Pt), palladium (Pd), rhodium (Rh), iridium (Ir), and/or osmium (Os). The alloy may contain about 10 atomic percent (at %) to about 75 at % of indium, and about 25 at % to about 90 at % of other elements. Any combination of one or more of the other elements is contemplated, though oxides are particularly contemplated.

The metal alloy may also be a tin alloy that contains indium in combination with elements such as oxygen, indium, nickel, cobalt, aluminum, chromium, molybdenum, niobium, titanium, tantalum, vanadium, rhenium, ruthenium, hafnium, tungsten, boron, yttrium, platinum (Pt), palladium (Pd), rhodium (Rh), iridium (Ir), and/or osmium (Os). The alloy may contain about 10 atomic percent (at %) to about 75 at % of tin, and about 25 at % to about 90 at % of other elements. Any combination of one or more of the other elements is contemplated, though oxides are particularly contemplated.

These metals can be used to provide physical and electrical property advantages when used with specific systems, such as electrochemical test strips. In such systems, the metal alloy conductive layer 30 can be processed to include at least one pattern formed from the alloy conductive layer. The pattern can be an electrode formed from the alloy conductive layer 30 by shadow masking, laser ablating, or lithography. The metal alloy conductive layer 30 can also be provided without any pattern formed thereon. That, the metal alloy conductive layer 30 can be provided with substantially continuous surfaces.

The metal alloy, such as a nickel-containing alloy, desirably exhibit improved physical and electrical properties. One improved property is the thickness of the metal alloy conductor layer, which can be very thin. In embodiments, the metal alloy conductor layer can have a thickness of about 10 nanometers to about 100 nanometers. Another improved property is the electrical conductivity of the conductor layer, which can be less than 100 ohms/square (Ω/sq) at the desired thickness. The metal alloy may also allow for improved stability, as measured by electrochemical response stability over time when exposed to humidity and temperature variations, or as measured by changes in adhesion and/or abrasion differences when exposed to a reagent. Other desirable properties can include physical contact durability, lowered contact resistance for lowered/more consistent bias response, and/or better cohesion for finer line formation in circuitry.

Physical and electrical properties which the metal alloy conductor layer provides may include thinness of the electrode, better electrical conductivity, stability over time, physical contact durability, lowered contact resistance for lowered/more consistent bias response, and/or better cohesion for finer line formation in circuitry.

To further increase the structural rigidity of the metal conductor layer 30, a TCO protective layer 40 can be formed on top of the metal layer. By capping the metal alloy layer 30, the TCO layer 40 adds mechanical robustness to the multilayer construct by increasing resistance to deformation of the metal conductor layer 30. A mechanical advantage from abrasion is also achieved with the protective TCO layer 40. The TCO protective layer is also highly electrically conductive, thus the conductivity of the overall multilayer construct is not affected. In addition, the multilayer construct may eventually include a chemical reagent layer. Thus, the TCO layer acts as a protective layer which provides chemical stability.

The TCO layer 40 can be coated onto the metal conductor layer 30 by any method known in the art, including planar magnetron sputtering, closed field magnetron sputtering, ion beam sputtering, rotatable magnetron sputtering, reactive thermal and electron beam evaporation, and CVD and PECVD processes. The protective TCO layer 40 can also be processed to include at least one pattern formed from the TCO layer. The pattern can be an electrode formed from the protective TCO layer 40 by shadow masking, laser ablating, or lithography. The at least one pattern formed from the TCO layer is substantially similar to that of the at least one pattern formed from the metal conductor layer 30. The TCO layer 40 can also be provided without any pattern formed thereon such that the TCO layer has substantially continuous surfaces.

TCO's have high optical transmission at visible wavelengths and electrical conductivity close to that of metals. An important feature of the TCO is that it is transparent while remaining electrically conductive. TCO's are generally n-type large band gap semiconductors with a relatively high concentration of free electrons in the conduction band, however, p-type materials are also contemplated. The wide bandgap provides for relatively high optical transmittance and free electrons increase electrical conductivity. To increase their conductivity, TCO's can be doped with donors (n-type) and acceptors (p-type). The TCO layer itself can be a binary, ternary, or quaternary compound. Examples include the most commonly used and widely developed TCO, indium tin oxide (ITO), which is Sn-doped indium oxide ($In_2O_3$). Other TCO examples include zinc oxide (ZnO), tin dioxide ($SnO_2$), cadmium oxide (CdO), tantalum oxide ($Ta_2O$), gallium indium oxide ($GaInO_3$), cadmium antimony oxide ($CdSb_2O_3$), titanium dioxide ($TiO_2$), tungsten trioxide ($WO_3$), molybdenum trioxide ($MoO_3$), and the like.

Generally, the TCO layer 40 comprises a large band gap semiconductor. To increase their conductivity, TCO's can be doped with donors (n-type) and acceptors (p-type). In one embodiment, the TCO layer 40 is indium tin oxide (ITO), which is an indium oxide ($In_2O_3$) semiconductor doped with Sn. Other embodiments of the present disclosure contemplate the use of other TCO's. In one embodiment, a zinc oxide (ZnO) semiconductor is doped with a suitable donor such as Al, Ga, B, In, Y, Sc, F, V, Si, Ge, Ti, Zr, Hf, Mg, As, H, and combinations thereof. In yet another embodiment, a tin dioxide ($SnO_2$) semiconductor is doped with a suitable donor such as Sb, F, As, Nb, Ta, and combinations thereof. In yet another embodiment, a cadmium oxide (CdO) semiconductor is doped with a suitable donor such as In or Sn. In yet another embodiment, a tantalum oxide ($Ta_2O$) semiconductor forms the TCO layer. In year another embodiment, a gallium indium oxide ($GaInO_3$) semiconductor is doped with a suitable donor such as Sn or Ge. In yet another embodiment, a $CdSb_2O_3$ semiconductor is used as the TCO layer. In yet another embodiment, a titanium dioxide ($TiO_2$) semiconductor is doped with a suitable donor such as $Ti^{2+}$ or $Ti^{3+}$. In yet another embodiment, a tungsten trioxide ($WO_3$) semiconductor is doped with a suitable donor such as $W^{3+}$, $W^{4+}$, or $W^{5+}$. In yet another embodiment, a molybdenum trioxide ($MoO_3$) semiconductor is doped with a suitable donor such as $Mo^{3+}$, $Mo^{4+}$, or $Mo^{5+}$.

These TCO's can be used to provide specific physical and electrical property advantages to the multilayer constructs disclosed herein, such as electrical conductivity and optical transparency, high physical density, low specific electrical resistance, high environmental and temperature stability, mechanical durability and solubility. The TCO protective layer 40 can provide these properties without adding thickness in specific systems, such as electrochemical test strips. In embodiments, the TCO protective layer can have a thickness of about 100 nanometers. Preferably, the TCO protective layer has a thickness of about 20 nanometers to about 50 nanometers.

At least two processes can be used for patterning the metal conductive layer 30 and the TCO protective layer 40, including in-line and off-line processes. In-line processing refers to a process which allows for fabrication of the pattern during deposition of the metal or TCO layer to the substrate. Off-line processing refers to a process wherein the metal or TCO is applied as a continuous layer over the substrate and subsequently removed to fabricate the pattern. The at least one pattern can be an electrode formed by at least three methods incorporating one of these processes.

In an in-line process, a shadow masking method uses a mask to control the deposition of the metal conductor layer on the substrate surface in a desired shape or footprint. This selective patterning is used to form the electrode. Put another way, the mask covers areas of the substrate on which the metal is not to be deposited, and exposes areas on which the metal is to be deposited. In this regard, the shadow masking method can be performed in-line during deposition of the metal layer itself. The shadow masking process can also be used to pattern the TCO layer.

In a second in-line process, a photolithographic method uses light to transfer a pattern from a photomask to a light-sensitive chemical resist on the substrate. The areas of the resist that have (or have not) been exposed are then developed by rinsing with an appropriate solvent to expose the substrate in the pattern. The metal conductor layer is then deposited on the exposed substrate to form one or more conductive patterns. This selective patterning is used to form the electrode.

In an off-line process, the metal is deposited to form a conductive layer on the substrate surface. Selective portions of this metal layer are then removed by laser ablation to form one or more patterns from the remaining portions of the conductive layer. The one or more patterns can be electrodes. The spectral response of the metal is very relevant as to which method (masked deposition versus laser ablation) is more preferable for a given metal.

The metal conductive layer and TCO protective layer having patterns or electrodes formed thereon can subsequently be used in a multilayer construct useful for forming an electrochemical test strip such as a biosensor.

The resulting pattern(s)/electrode(s) formed from the layers desirably exhibit improved physical and electrical properties. One improved property is the thickness of the electrode, which can be very thin. In embodiments, the electrode can have a thickness of about 10 nanometers to about 100 nanometers. Another improved property is the electrical conductivity of the electrode, which can be less than 100 ohms/square ($\Omega$/sq) at the desired thickness. The biosensor may also exhibit improved stability, as measured by electrochemical response stability over time when exposed to humidity and temperature variations, or as measured by changes in adhesion and/or abrasion differences when exposed to the reagent. Other desirable properties can include physical contact durability, lowered contact resistance for lowered/more consistent bias response, and/or better cohesion for finer line formation in circuitry.

The resulting multilayer construct formed from the substrate, conductive metal alloy layer, and TCO protective layer desirably exhibit improved physical and electrical properties. One improved property mechanical robustness of the multilayer construct while improving or maintaining an adequate electrical conductivity across the electrodes. The multilayer construct may also exhibit improved stability, as measured by electrochemical response stability over time when exposed to humidity and temperature variations, or as measured by changes in adhesion and/or abrasion differences when exposed to the reagent. Other desirable properties can include physical contact durability, lowered contact resistance for lowered/more consistent bias response, ease of transportation and handling, reduced cost, and/or better cohesion for finer line formation in circuitry.

A specific description of the equipment and processes used to construct the multilayer construct referred to will now be described with reference to FIG. 2. The machine 110 will produce the multilayer constructs previously described at high speed in a single pass. The machine 110 has a rotary drum 120 capable of rotating in a clockwise direction, as indicated by the arrow. Rotary drum 120 rotates and unwinds substrate 132, which can be stored as an unwind roll 130. As explained above, most desirably the metal conductor layer is formed by sputtering onto the substrate as a thin film. Initially, the substrate surface 132 can be processed before the thin film is deposited. As the substrate 132 is conveyed from the unwind roll 130, it passes RF pretreater 140 which treats the substrate with a plasma, to achieve better adhesion between the substrate layer and the thin film metal conductor layer. This can mean processing only a portion of the substrate 132 where the thin film is to be deposited, or the entire substrate can be processed. Specifically, the substrate surface 132 can be plasma treated with argon, which can be either pure argon or a mixture of argon with a secondary gas. The secondary gas can be a reactive gas, such as oxygen, nitrogen, methane, perfluoromethane, and other suitable gases. The secondary gas can be present in an amount of 5% to 100% (v/v), balance argon. The plasma treatment causes surface effects on the substrate surface. No wet treatment is used.

After passing the Radio Frequency (RF) plasma pretreater 140, the substrate enters chamber 150, passes through the chamber and is eventually wound onto roll 190. After the desired quantity of film is treated, the Radio Frequency (RF) pretreater is stopped along with the substrate travel. The first portion of chamber 150 is a metal sputtering zone 160. Metal sputtering zone 158 contains two planar cathodes 160 which may be operated as a dual cathode DC sputtering option, or may be used to produce a mixed metal layer, as desired.

In sputtering the thin film onto the substrate 132, a sputtering target is bombarded with energetic particles, and atoms ejected from the sputtering target are deposited onto the substrate to form the thin film. The composition of the sputtering target itself can affect the microstructure of the deposited thin film. Thus, controlling the grain size, gas content entrainment, and target density of the sputtering target is performed. Further fine control can be accomplished through varying the sputtering pressure through the normal range of about 0.5 milliTorr (mTorr) to about 5 mTorr. Argon is usually used as the main sputtering gas. However, other gases can be added to the argon, for example a content level of from about 1% to about 20% of nitrogen, neon, helium, krypton, methane, perfluoroethane, or another suitable gas. These gases will create differing morphologies by fine tuning the deposition rate, from a larger structure using krypton gas (highest deposition rate) to 20% helium (lowest deposition rate, but finest structure).

Upon completion of the depositing of the conductive layer, the substrate then travels through the seal into the second sputtering zone for depositing the TCO layer. A dual rotary cathode 154 performs reactive AC sputtering of the TCO layer on the thin film metal conductor layer.

The dual rotary cathode 154 is designed to have low conductance seals to allow for reactive sputtering of a TCE at high speeds for long runtimes. The dual rotary cathode 154 runs longer, cleaner, and more consistently compared to planar cathode technology. In this regard, the dual rotary cathode 154 uses inert gases mixed with reactive gases but with the use rotary cathodes to achieve a cleaner atmosphere and target surface can be achieved.

As noted above, after depositing the thin film metal conductor layer, the substrate 132 passes to the TCO sputtering zone 152. Metal sputtering zone 158 and TCO sputtering zone 152 are separated from each other by seal 156. In the TCO sputtering zone 152, the thin film can be plasma treated with argon, which can be either pure argon or a mixture of argon with a secondary gas. The secondary gas can be a reactive gas, such as oxygen, nitrogen, methane, perfluoromethane, and other suitable gases. The secondary gas can be present in an amount of 5% to 100% (v/v), balance argon. AC reactive sputtering 152 then deposits the protective TCO layer on top of the thin film metal conductor layer. The substrate 132, having thin film metal conducting layer and protective TCO layer deposited thereon, exits the chamber. Measuring unit 180 can then measure the optics and resistance of the layers in-line with the processes previously discussed. Takeup roll 190 removes substrate 132 from the rotary drum for subsequent processing.

The high speed single pass process described above with respect to machine 110 can process substrate polymer web material having a width of about 30 inches and a length about 2000 to about 3000 feet. The sputtering processes discussed above can be performed at a high rate of about 10 ft/min to about 15 ft/min.

The machine described above desirably produces the multilayer constructs disclosed herein at high speed in a single pass, compared with multilayer constructs prepared by other multi-pass methods. Low conductance seals advantageously permit the deposition of both the thin film metal layer and the TCO protective layer at once, in one chamber, at a relatively high-speed.

The present disclosure is further illustrated in the following non-limiting working examples, it being understood that these examples are intended to be illustrative only and that the disclosure is not intended to be limited to the materials, conditions, process parameters and the like recited herein.

EXAMPLE 1

A conductive layer was formed by sputtering gold onto a surface of a substrate. A protective TCO layer was formed on top of the conductive layer by sputtering ITO on the gold conductive layer. Table 1 below lists the target thicknesses for the gold conductive layer and the ITO layer, along with the resultant resistivities observed. The resistances represent the average measured surface resistance across five test points.

TABLE 1

Target thicknesses and resultant surface resistances of Gold/ITO multilayer construct.

| Target Thickness - Gold Angstroms (Å) | Target Thickness - ITO Angstroms (Å) | Surface Resistance Ohms/sq. (Ω/sq.) |
|---|---|---|
| 200 | * | 4.33 |
| 250 | 600 | 2.98 |
| 250 | 300 | 3.26 |
| 75 | 600 | 13.26 |
| 75 | 300 | 14.35 |

EXAMPLE 2

A conductive layer was formed by sputtering palladium onto a surface of a substrate. A protective TCO layer was formed on top of the conductive layer by sputtering ITO on the palladium conductive layer. Table 2 below lists the target thicknesses for the palladium conductive layer and the ITO layer, along with the resultant resistivities observed. The resistances represent the average measured surface resistance across five test points.

TABLE 2

Target thicknesses and resultant surface resistances of Palladium/ITO multilayer construct.

| Target Thickness - Palladium Angstroms (Å) | Target Thickness - ITO Angstroms (Å) | Surface Resistance Ohms/sq. (Ω/sq.) |
|---|---|---|
| 150 | 300 | 23.4 |
| 400 | 300 | 5.91 |
| 400 | 600 | 5.4 |
| 150 | 600 | 19.0 |

EXAMPLE 3

A conductive layer was formed by sputtering titanium onto a surface of a substrate. A protective TCO layer was formed on top of the conductive layer by sputtering indium zinc oxide (IZO) on the titanium conductive layer. Table 2 below lists the target thicknesses for the palladium conductive layer and the ITO layer, along with the resultant resistivities observed.

TABLE 3

Target thicknesses and resultant surface resistances of Titanium/IZO multilayer construct.

| Target Thickness - Titanium Angstroms (Å) | Target Thickness - IZO Angstroms (Å) | Surface Resistance Ohms/sq. (Ω/sq.) |
|---|---|---|
| 200 | 300 | 52.5 |
| 200 | 200 | 60 |
| 300 | 100 | 42 |
| 400 | 100 | 30 |

The present disclosure has been described with reference to the exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An electrochemical test strip comprising a multilayer construct including:
   a substrate layer having a top surface and a bottom surface,
   a metal conductor layer deposited onto the top surface of the substrate layer, and
   a protective layer deposited onto a top surface of the conductor layer, wherein the protective layer is a transparent conducting oxide;
   wherein a pattern is formed from the metal conductor layer; and
   wherein the protective layer has substantially continuous surfaces without any pattern formed therein.

2. The multilayer construct of claim 1, wherein the pattern is formed in-line by masked deposition, in-line by lithography, or off-line by laser ablation.

3. The multilayer construct of claim 2, wherein the pattern is formed by placing a mask on the top surface of the substrate in a desired shape, wherein the mask covers the areas of the substrate on which the metal conductor layer is not to be deposited, and exposes areas on which the metal conductor layer is to be deposited followed by the deposition of the metal conductor layer to form an electrode.

4. The multilayer construct of claim 1, wherein the bottom surface of the substrate layer is free of additional conductive layers.

5. The multilayer construct of claim 1, wherein the metal conductor layer is a pure metal or metal alloy.

6. The multilayer construct of claim 5, wherein the metal is a nickel-based alloy, a cobalt-based alloy, an indium-based alloy, or a tin-based alloy.

7. The multilayer construct of claim 1, wherein the transparent conducting oxide is selected from the group including indium tin oxide (ITO), zinc oxide (ZnO), tin dioxide ($SnO_2$), cadmium oxide (CdO), tantalum oxide ($Ta_2O$), gallium indium oxide ($GaInO_3$), cadmium antimony oxide $CdSb_2O_3$), titanium dioxide ($TiO_2$), tungsten trioxide ($WO_3$), and molybdenum trioxide ($MoO_3$).

8. The multilayer construct of claim 1, further including a reagent layer deposited onto the protective transparent conducting oxide layer and an optional cover layer.

9. The multilayer construct of claim 1, wherein the substrate layer is a non-conductive polymer web.

10. The multilayer construct of claim 9, wherein the non-conductive polymer web is selected from the group consisting of polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, polystyrene, and combinations thereof.

11. A method of forming an electrochemical test strip having a multilayer construct, comprising:
   processing a surface of a substrate layer to obtain a processed substrate;
   depositing a metal conductor layer onto the processed substrate,
   forming a pattern in the metal conductor layer; and
   depositing a protective transparent conductive oxide layer onto the metal conductor layer, wherein the protective transparent conductive oxide layer has substantially continuous surfaces without any pattern formed therein.

12. The method of claim 11, wherein the substrate surface is processed by plasma treatment.

13. The method of claim 11, wherein the metal conductor layer and the protective transparent conductive oxide layer are deposited by AC reactive sputtering.

14. The method of claim 13, wherein the AC reactive sputtering is produced by a dual rotary cathode.

15. A system comprising:
   an electrochemical test strip with
   (1) a substrate layer having a top surface and a bottom surface;
   (2) a metal conductor layer formed on the top surface of the substrate layer; and
   (3) a protective layer deposited on top of the conductor layer comprising a transparent conductive oxide; and
   a measuring device;
   wherein a pattern is formed from the metal conductor layer; and
   wherein the protective layer has substantially continuous surfaces without any pattern formed therein.

* * * * *